United States Patent [19]

Kardjian

[11] Patent Number: 6,010,447
[45] Date of Patent: Jan. 4, 2000

[54] BLADDER SLING

[76] Inventor: Paul M. Kardjian, 4318 Hawthorne Dr., Vernon, N.Y. 13476

[21] Appl. No.: 09/127,214

[22] Filed: Jul. 31, 1998

[51] Int. Cl.⁷ .................................. A61F 2/00; A61F 5/00
[52] U.S. Cl. .................................... 600/29; 128/DIG. 25; 602/4
[58] Field of Search ................. 600/30, 29, 37; 602/4, 75, 34, 32; 128/DIG. 25; 623/12; 601/153; 606/72, 151, 213, 226, 232

[56] References Cited

U.S. PATENT DOCUMENTS

| | | | |
|---|---|---|---|
| 2,847,002 | 8/1958 | Doumar | 602/4 |
| 3,750,658 | 8/1973 | Dawson, Jr. et al. | 602/32 X |
| 4,857,041 | 8/1989 | Annis et al. | 600/30 |
| 5,013,292 | 5/1991 | Lemay | 600/30 |
| 5,334,217 | 8/1994 | Das | 606/213 |
| 5,368,602 | 11/1994 | de la Torre | 606/151 |
| 5,658,245 | 8/1997 | McGinnis et al. | 602/32 |
| 5,840,011 | 11/1998 | Londgrebe et al. | 600/30 |

*Primary Examiner*—Richard J. Apley
*Assistant Examiner*—Denise Pothier
*Attorney, Agent, or Firm*—George R. McGuire

[57] ABSTRACT

A sling device for implant in a human body as a bladder support includes a rectangular, flexible strip of cloth with stiffening members extending across each of the two shorter sides. The stiffening members at each end include a pair of spaced, parallel beams, integrally connected at their ends. Marginal end portions of the flexible strip are passed through the space between the beam around one of the beams, and folded back upon and affixed to the opposing surface of the flexible strip. A flexible suture is attached to a loop at the midpoint of the other beam.

3 Claims, 3 Drawing Sheets

6,010,447

BLADDER SLING

BACKGROUND OF THE INVENTION

The present invention relates to apparatus for use as a sling to support the bladder in a position calculated to relieve female urinary stress incontinence. More specifically, the invention relates to a device in the nature of a flexible sling which is positioned by a surgeon below a patient's bladder, with sutures extending from opposite sides of the sling anchored to the pubic bone.

The prior art includes sling devices for supporting internal body organs. Such slings have included rectangular strips of biologically compatible material with surgical thread attached to each side of the strip for anchoring to the abdominal wall or the pubic bones. However, the flexible strip has a tendency to bunch up along the longitudinal axis, thereby in effect becoming narrower and less suited to perform its supporting function.

It is a principal object of the present invention to provide an implantable device in the nature of a bladder-supporting sling with long-term performance superior to that of prior art devices of this type.

It is a further object to provide a bladder sling for alleviation of female urinary stress incontinence including a flexible strip of material with sutures extending from opposite sides for attachment to an anchoring body part wherein the strip does not tend to fold or bunch along the longitudinal axis, thereby reducing the effective width of the strip.

Other objects will in part be obvious and will in part appear hereinafter.

SUMMARY OF THE INVENTION

Briefly stated, the device of the invention includes a rectangular, biological compatible strip of flexible material with each of the short sides supported by a rigid or semi-rigid strut. An eyelet, or the like, is provided at the center of each strut for passage of a surgical thread which is anchored to the inside of the abdominal wall or proximate bone structure such as the pubic bone. The struts provide support for the lateral edges of the sling material, effectively preventing the latter from folding or bunching toward the center in a manner tending to reduce the supporting area of the sling.

The foregoing and other details of construction and use of the device will be more readily understood and fully appreciated from the following detailed disclosure, taken in conjunction with the accompanying drawings.

DETAILED DESCRIPTION

Figure 1:
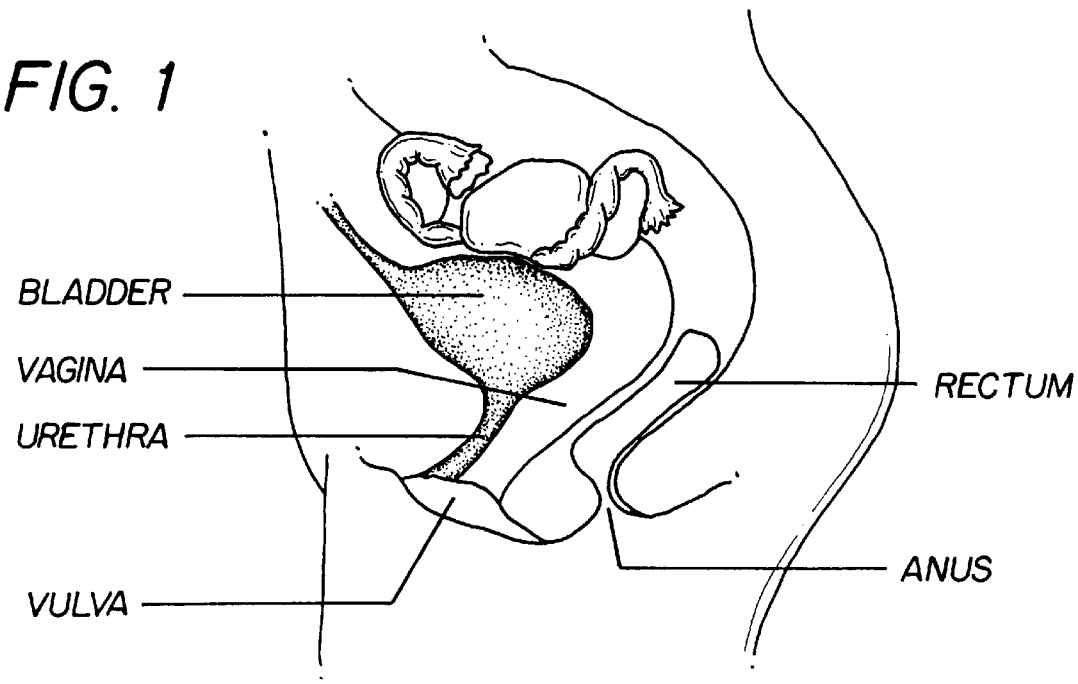
FIG. 1 is a somewhat diagrammatic, lateral section of a female body in the lower torso region showing various internal organs in normal positions.
Figure 2:
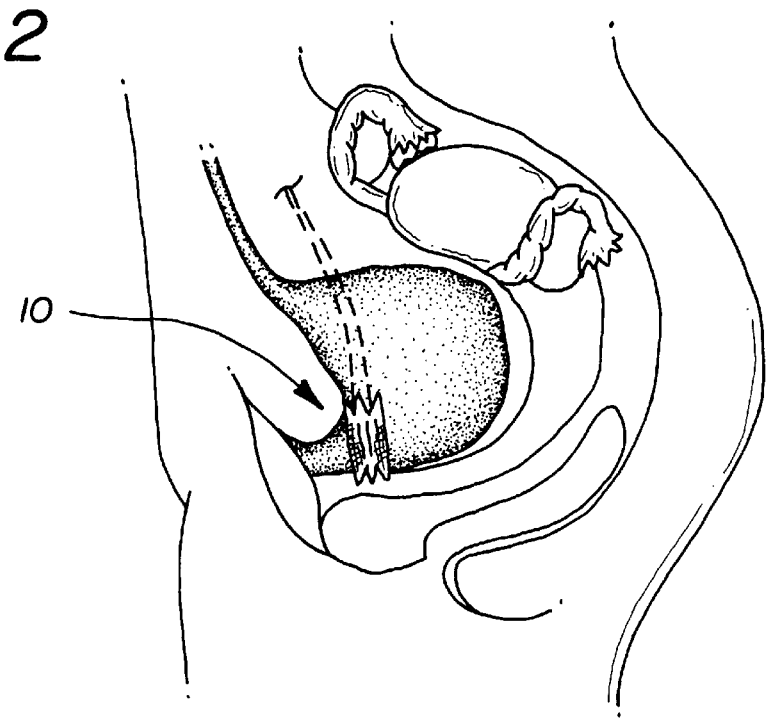
FIG. 2 is the same view as FIG. 1 with the internal organs in a "dropped" position, which is common in many women after repeated childbirths and/or with advancing age, and with the sling device of the present invention positioned under the bladder.

Referring now to the drawings, in FIG. 1 is shown, for reference purposes, a lateral section of the lower part of a female torso with various, labeled anatomical parts in normal positions. FIG. 2 illustrates the same portion of the anatomy with internal organs positioned substantially as they would be in a subject with a so-called dropped uterus. It will be noted that the bladder is considerably lowered from its normal position, and the urethra is compressed and foreshortened, resulting in a condition known as female urinary stress incontinence. Among the measures undertaken to alleviate this condition are implanted devices in the nature of slings for providing support to the dropped bladder. A prior art sling, denoted generally by reference numeral 10, is shown in FIG. 2 in supporting position substantially at the junction of the bladder and urethra.

Figure 3:
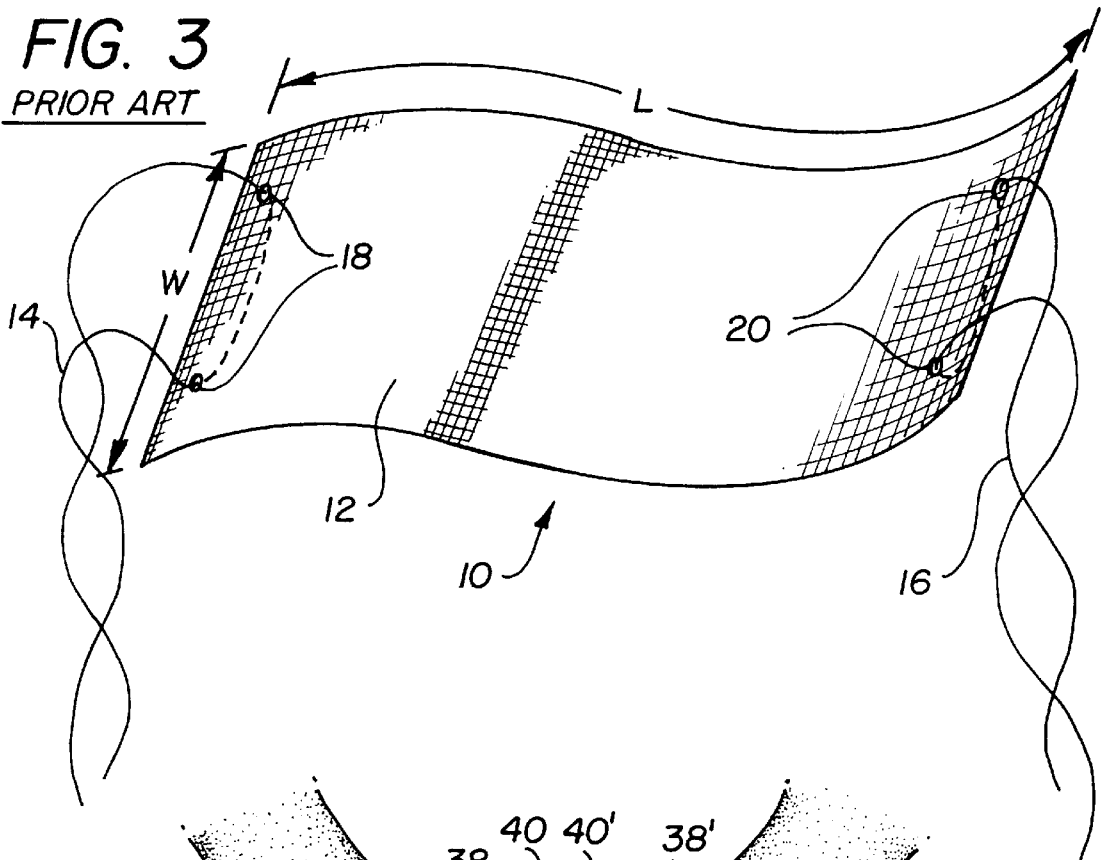
FIG. 3 is a perspective view of a typical prior art bladder sling.

Sling 10, as shown separately in FIG. 3, consists of rectangular strip 12 of flexible, biologically compatible material such as that commercially available under the Trademark Protegen, from Microvasive/Boston Scientific, and surgical threads 14 and 16 passing through openings 18 and 20, respectively, along the shorter sides of strip 12. Sling 10 is normally implanted in a procedure wherein strip 12 is properly positioned and the ends of threads 14 and 16 remote from strip 12 anchored, typically to the interior of the abdominal wall, by a surgeon. The length and width of strip 12 are indicated as L and W, respectively, in FIG. 3. It will be noted that the supporting strip portion of sling 10 is illustrated in FIG. 2 as being folded or bunched toward the longitudinal centerline of the strip, a condition which commonly develops after the sling has been in position for some length of time. This condition, known as "accordioning," effectively reduces the width of the strip with concomitant reduction in its supporting capability, and creating complications.

Figure 5:
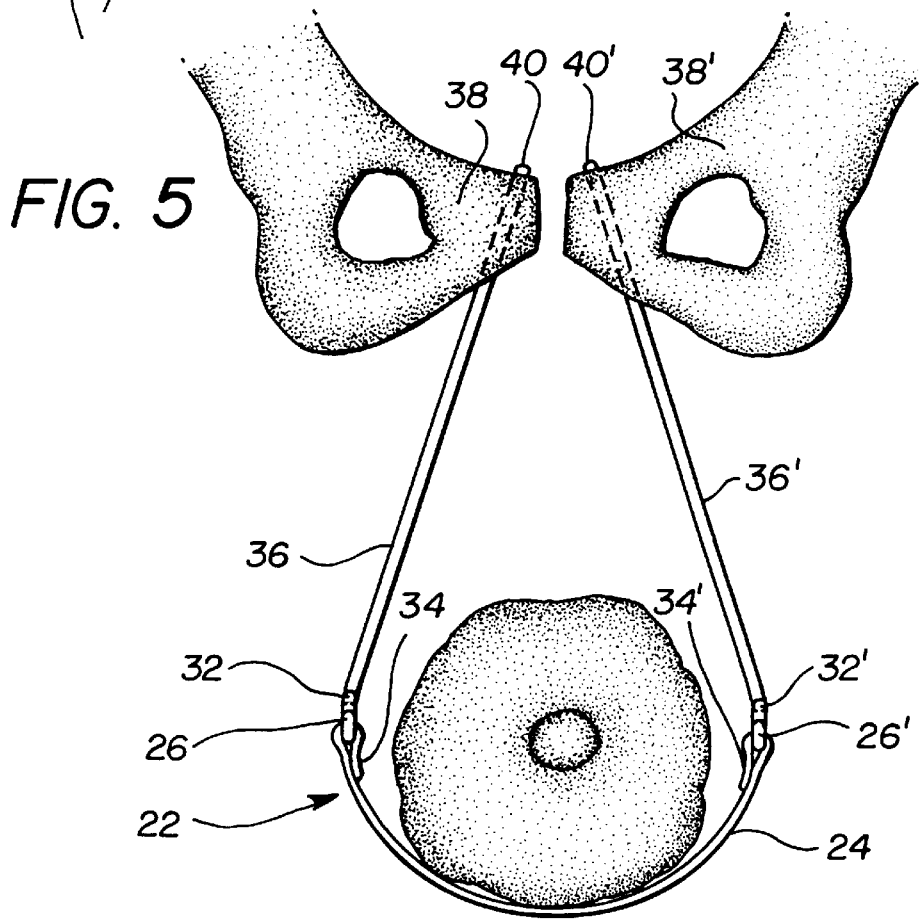
FIG. 5 is an elevational view of the sling of the invention shown in supporting relation to a bladder and anchored to bone structure.
Figure 4:
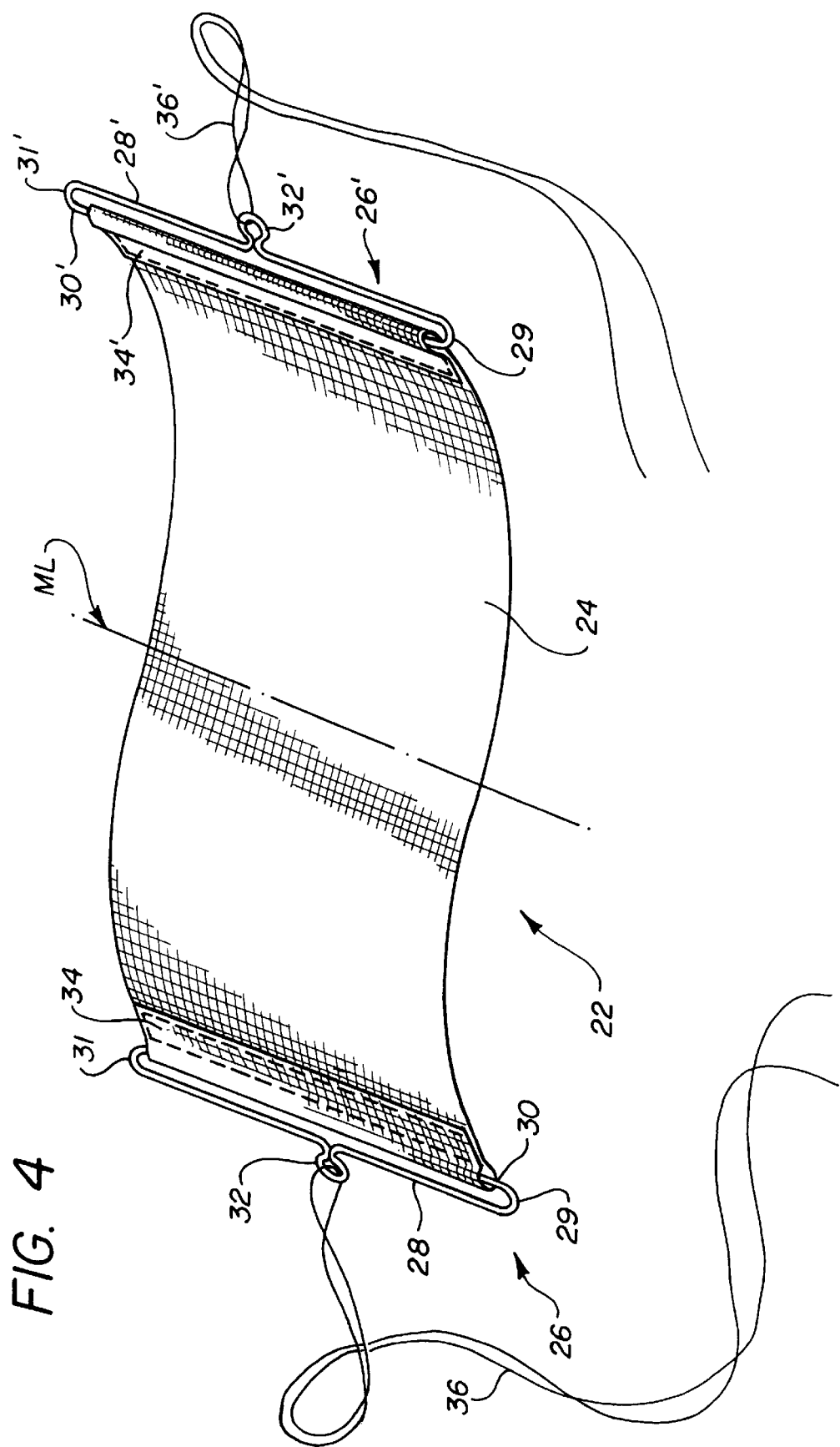
FIG. 4 is a perspective view of the bladder sling of the present invention.

Turning now to FIGS. 4 and 5, the sling of the present invention, denoted generally by reference numeral 22, is shown in perspective view and in supporting relation to a bladder/urethra, respectively. Sling 22 includes rectangular strip 24 and end struts 26, 26'. Strip 24 may be of the same dimensions and material as strip 12 of prior art sling 10. End struts 26, 26' are of identical construction, preferably being one-piece moldings of a rigid or semi-rigid plastic suitable for anatomical implantation. Strut 26 includes spaced, parallel beams 28 and 30, joined at their ends by curved portions 29, 31. Eyelet or loop 32 is integrally formed in beam 28 at the midpoint thereof. Structurally identical portions of strut 26' are indicated by reference numerals applied to corresponding portions of strut 26 with a prime sign added.

Strip 24 is secured along its opposite, shorter edges to struts 26 and 26' by passing the edges of the strip through the spaces between the beams of the struts and securing opposing faces of the strip together. That is, in the illustrated embodiment, one of the shorter edges of strip 24 is passed through the space between beams 28 and 30 to provide marginal portion 34 which is stitched, heat sealed, or otherwise secured to the underlying, opposing face of strip 24. The opposite, shorter edge of strip 24 is likewise passed through the space between beams 28' and 30', with marginal portion 34' secured to the opposing surface of the strip.

Sutures 36 and 36' are passed through loops 32 and 32', respectively, and sling 22 is implanted and positioned in the desired relationship to the bladder by the surgeon. Sutures 36 and 36' are then secured to appropriate portions of the anatomy to anchor the sling in the desired position. For example, as shown in FIG. 5, sutures 36, 36' are anchored to portions 38, 38' of the pubic bone and may be secured in the areas denoted by reference numerals 40, 40' by appropriate surgical clips, or the like.

Strip 24, being thus supported along its shorter sides by struts 26, 26' does not exhibit the accordion effect commonly encountered in flexible strips of prior art slings. Accordingly, sling 22 is easier to install and performs its intended function more efficiently than comparable prior art bladder slings. In addition, complications such as erosion and urinary retention due to the accordion effect are also avoided by this invention. Modifications of the invention within the scope of the appended claims are contemplated. For example, rather than securing the ends of the strip to the struts by looping the strip material around one of the strut beams, as shown, the strip material may be fixedly attached along part or all of its shorter side(s) to one or more strut beams by an adhesive, heat sealing, or other appropriate means. Although a single loop at the center of each strut is provided for the sutures, two or more loops or similar structure for engagement of the sutures with the struts may be provided.

What is claimed is:

1. An bladder sling for implant in a human anatomy to alleviate female urinary stress incontinence, said sling comprising:

a) a substantially rectangular, flexible strip of material having two longer and two shorter sides:

b) stiffening means extending along each of said shorter sides, said stiffening means at each of said shorter sides comprising first and second, substantially rigid beams extending in spaced, substantially parallel relation between opposite ends which are joined to form a unitary, one-piece structure;

c) marginal edge portions of said strip along each of said shorter sides passing through the space between said first and second beams, around said first and second beams and affixed to said strip;

d) a pair of flexible sutures; and e) means for attaching one of said sutures to said second beam at each of said shorter sides of said strip substantially at the midpoint between said opposite ends of said second beam.

2. The sling of claim 1 wherein said means for attaching said sutures comprises at least one loop for passage therethrough of said suture.

3. The sling of claim 1 wherein said means for attaching said sutures comprises a single loop formed in said second beam at said midpoint between said opposite ends of said second beam.

* * * * *